United States Patent [19]

Nakada et al.

[11] Patent Number: 5,532,418
[45] Date of Patent: Jul. 2, 1996

[54] METHOD OF PRODUCING 1,1,1,2,3,3,-HEXAFLUOROPROPANE AND TETRAFLUOROCHLOROPROPENE

[75] Inventors: Tatsuo Nakada; Hirokazu Aoyama, both of Settsu, Japan

[73] Assignee: Daikin Industries Ltd., Osaka, Japan

[21] Appl. No.: 392,906

[22] PCT Filed: Aug. 9, 1993

[86] PCT No.: PCT/JP93/01117

§ 371 Date: Mar. 1, 1995

§ 102(e) Date: Mar. 1, 1995

[87] PCT Pub. No.: WO94/05611

PCT Pub. Date: Mar. 17, 1994

[30] Foreign Application Priority Data

Sep. 4, 1992 [JP] Japan ................... 4-262863

[51] Int. Cl.[6] ............... C07C 17/08; C07C 17/25
[52] U.S. Cl. ............ 570/166; 570/156; 570/168
[58] Field of Search ................ 570/156, 166, 570/168

[56] References Cited

U.S. PATENT DOCUMENTS

| | | | |
|---|---|---|---|
| 2,900,423 | 8/1959 | Smith | 570/156 |
| 5,396,000 | 3/1995 | Nappa et al. | 570/156 |

FOREIGN PATENT DOCUMENTS 9325510  12/1993  WIPO ................ 570/156

*Primary Examiner*—Alan Siegel
*Attorney, Agent, or Firm*—Armstrong, Westerman, Hattori, McLeland & Naughton

[57] ABSTRACT

A method of producing 1,1,1,2,3,3-hexafluoropropane in a characteristic process in which tetrafluorochloropropene is first obtained from the dechlorofluorination (removing ClF) of 1,1,1,2,2-pentafluoro-3,3-dichloropropane and/or 1,1,2,2,3-pentafluoro-1,3-dichloropropane by hydrogen in the presence of a metal oxide catalyst and then the product olefin is fluorinated in the presence of a catalyst. By this method, 1,1,1,2,3,3-hexafluoropropane, which is useful as an action fluid and so on and has a property to help preserving the environment, and an intermediate in its synthesis can be easily produced at low cost.

4 Claims, No Drawings

METHOD OF PRODUCING 1,1,1,2,3,3,-HEXAFLUOROPROPANE AND TETRAFLUOROCHLOROPROPENE

This application is a 371 of PCT/JP93/01117 filed 8/9/93

1. Industrial fields where the invention can be utilized.

This invention relates to a method of producing 1,1,1,2,3,3-hexafluoropropane at low cost, which is a hydrofluorocarbon having no fear of destroying ozone layer and may be substituted for chlorofluorocarbons which have been used as working fluids and blowing agents, and also relates to a method of producing tetrafluorochloropropene, an intermediate in the synthesis of 1,1,1,2,3,3-hexafluoropropane.

2. Prior art

Until now, 1,1,1,2,3,3-hexafluoropropane is known to be obtained by hydrogenation of hexafluoropropene. However, hexafluoropropene as a raw material is expensive. Therefore, the fluoropropane produced by the process of using hexafluoropropene as a raw material is inevitable to be expensive and its applications are limited.

OBJECTS OF THE INVENTION

This invention is aimed at offering a method of easily producing 1,1,1,2,3,3-hexafluoropropane at low cost, which is useful as a working fluid and so on and has a property to help preserving the environment, and an intermediate in its synthesis.

The constitution of the invention.

As a result of eagerly studying of the process of producing 1,1,1,2,3,3-hexafluoropropane efficiently and at low cost, the inventor found a process in which 1,1,1,2,3,3-hexafluoropropane is derived at high selectivity from 1,1,1,2,2-pentafluoro-3,3-dichloropropane and/or 1,2,2,3-Pentafluoro-1,3-dichloropropane which are available at low cost, having reached this invention.

That is, this invention relates to a method of producing 1,1,1,2,3,3-hexafluoropropane in a characteristic process in which tetrafluorochloropropene is first obtained from dechlorofluorinating (removing ClF) 1,1,1, 2,2-pentafluoro-3,3-dichloro propane and/or 1,1,2,2,3-pentafluoro- 1,3-dichloropropane by hydrogen in the presence of a metal oxide catalyst and then the product olefin is fluorinated in the presence of a catalyst.

This invention also offers a method of producing tetrafluorochloropropene as an intermediate in the synthsis of the above-mentioned 1,1,1,2,3,3-hexafluoropropane which is characteristic of dechlorofluorinating (removing ClF) 1,1,1,2,2-pentafluoro-3,3-dichloropropane and/or 1,1,2,2,3-pentafluoro-1,3-dichloropropane by hydrogen in the presence of a metal oxide catalyst.

In the production process of this invention, a metal oxide catalyst used in the above-mentioned dechlorofluorination reaction is desirable to be consisted of the oxides of one or more than one kind of metals selected from iron (Fe), chromium (Cr), and copper (Cu).

And a catalyst of fluorinating the above-mentioned tetrafluorochloropropene is desirable to be fluoride or oxyfluoride of chromium (Cr) or aluminum (Al).

And the above-mentioned raw materials, 1,1,1,2,2-pentafluoro- 3,3-dichloropropane and 1,1,2,2,3-pentafluoro1,3-dichloropropane are preferable to be reacted in a mixture.

The invention Will be explained in detail.

At first, the raw materials, 1,1,1,2,2-pentafluoro-3,3-dichloropropane and/or 1,1,2,2,3-pentafluoro-1,3-dichloropropane are known to be easily obtained at low cost, in general, by the reaction of dichlorofluoromethane and tetrafluoroethylene.

And when the raw materials obtained from the above reaction are reduced with hydrogen by using a metal oxide as a catalyst found in this invention, chlorine and fluorine in the raw materials are separated and 1,1,1,2-tetrafluoro-3-chloro 2-propene is given in case of 1,1,1,2,2-pentafluoro3,3-dichloropropane, similarly two kinds of isomers of 1,1,2,3-tetrafluoro-1-chloro-2-propene and 1,1,1,2,3-tetra-fluoro- 3-chloro-1-propene are given in case of 1,1,2,2,3-pentafluoro- 1,3-dichloropropane.

Then, 1,1,1,2,3,3-hexafluoropropane is synthesized by fluorinating thus obtained olefins (tetrafluorochloropropenes) by using, for instance, hydrogen fluoride in the presence of a catalyst.

The inventor discovered suitable catalysts for the above-mentioned dechlorofluorination (removing ClF) and fluorination reactions, and further found that as a result of studying of the both reactions' conditions, particularly 1,1,1,2,3,3-hexafluoropropane is selectively obtained when the mixture of 1,1,1,2,2-pentafluoro-3,3-dichloropropane and 1,1,2,2,3-pentafluoro-1,3-dichloropropane itself is used as a raw material of the reaction, and have completed this invention.

In the above-mentioned reaction of dichlorofluoromethane and tetrafluoroethylene, 1,1,2,2,3-pentafluoro-3,3-dichloropropane and 1,1,2,2,3-pentafluoro-1,3-dichloropropane are obtained as s mixture of isomers.

Therefore, it is the most advantageous in the production cost to use the mixture as a raw material, and the primary advantage of this process is that even if a mixture of isomers is used, the object compound 1,1,1,2,3,3-hexafluoropropane is selectively obtained. However, it is also acceptable to use each isomer alone as a raw material for the reaction after separating the mixture of isomers. It is also possible to use each compound as a raw material after synthsizing them by different processes.

Metal oxides, which are used as catalysts in the reduction dehalogenation (dechlorination and defluorination with hydrogen) of 1,1,1,2,2,-pentafluoro-3,3-dichloropropane and 1,1,2,2,3-pentafluoro-1,3-dichloropropane, can be obtained by burning of metal hydoxides which are precipitated when the alkali of ammonium aqueous solution or an alkaline metal hydroxide is added to an aqueous solution of chlorides, sulfates or nitrates of Fe, Cr, and Cu in an usual manner.

Though each of these metal oxides is possible to be used alone, the multiple oxide or the mixture of oxides of more than one metal selected from these metals (Fe, Cr, Cu) are also acceptable.

These metal oxides can be used in compressed pellets as well as in granular form. They also can be used in being carried on such carriers as active carbon, aluminum fluoride, and silica gels which do not take part in the reaction directly.

As for excessive ratio of hydrogen used in the above-mentioned dechlorofluorination, the reaction can be carried out when hydrogen is more than 1 molar amount to the necessary raw material, but it is practically desirable to be over 1.5 times. As much excessive hydrogen makes contact time short to reduce conversion rate, it is practical to be reacted at about 2 molar ratio. However, even if hydrogen amount is much excessive, the reaction can be carried out when it is possible to use a larger reactor, larger amount of catalyst, and a longer contact time.

The reaction temperature of the reduction dehalogenation of 1,1,1,2,2-pentafluoro-3,3-dichloropropane and 1,1,2,2,-pentafluoro-1,3-dichloropropane can be properly selected from the range of 200° to 400° according to the activity of a catalyst used. As generally known, the reaction velocity increases when the reaction temperature is raised, so a high reaction temperature is needed in case of using a catalyst of low activity. However, if the reaction temperature is over 400°, the production ratio of C2 and C4 compounds, that are considered to be the products of the cleavage and bonding of C—C bonds, is apt to increase, causing the selectivity to lower.

A contact time can be properly determined by selecting a catalyst activity and a reaction temerature in accordance with an intended conversion rate. In general, when a catalyst activity is low, a proper conversion rate can be set by selecting a long contact time.

As for catalysts used in the above-mentioned fluorination of tetrafluoropropene, chromium fluoride and aluminum fluoride produced by fluorinating $Cr_2O_3$, or $Al2O_3$ with hydrogen fluoride, or chromium oxyfluoride and aluminum oxyfluoride are applicable. These can be used in pellets as well as in granular form. And they also can be used in being carried on carriers which do not take part in the reaction directly.

$Cr_2O_3$ and $Al_2O_3$ may be prepared through processes in which an appropriate base such as ammonia aqueous solution and alkaline metal salts is added to each metal's nitrate, sulfate, or chloride.

The reaction temperature of the fluorinating reaction is generally from 200° to 400°, preferablly from 280° to 350°, and can be optionally determined at will as well as the contact time according to the required selectivity and conversion.

About HF that is used as a fluorinating reagent, the fluorination reaction proceeds when the amount of HF is more than 2 times that of the feed mateiral tetrafluorochloropropene in mole ratio. It is preferable to feed HF excessively in order to obtain proper conversions. However, the greater the excessive rate of HF is, the higher the cost of recycling HF becomes. Therefore, it is preferable to keep from 3 to 10 times, most preferablly from 5 to 8 times in mole ratio.

The possibility of utilizing the invention in industry

In the method of this invention, 1,1,1,2,2-pentafluoro3,3-dichloropropane and/or 1,1,2,2,3-pentafluoro-1,3-dichloropropane which are available at low cost are dechlorinated and defluorinated (removing ClF) with hydrogen in the presence of a catalyst of metal oxide to produce tetrafluorochloropropene, and then the product olefin is fluorinated in the presence of a catalyst. Therefore, 1,1,1,2,3,3-hexafluoropropane, which doesn't cause environmental disruption (has a property to help preserving the environment) and is useful, and an intermediate in its synthesis are easily obtained at high selectivity and low cost.

Embodiments

The invention will be explained more concretely in the following examples.

EXAMPLE 1.

120 g of $Cr(NO_3)_3.9H_2O$ was disolved in 250 ml of water, and then its hydroxide precipitation was formed by adding this solution and 200 ml of 28% ammonium hydroxide aqueous solution to 400 ml of heated water with stirring them. This precipitation was separated by filtration, then washed with pure water followed by drying, and finally burnt at 450° C. for 5 hours to produce the powder of oxide (chromium oxide). The powder was molded into a cylindrical shape, 5 mm of diameter and 5 mm of height, by using a tapping-type molding machine.

10 g of the aforesaid chromium oxide was filled in a reactor made of Hastelloy-C (20 mmφ×1000 mm) and set at the reaction temperature. A pretreatment was made by passing hydrogen at a rate of 200 ml/min. for 3 hours in advance. Then 1,1,1,2,2-pentafluoro-3,3-dichloropropane was introduced at a rate of 100 ml/min. after being vaporized in a vaporizer.

The products were analyzed by a gas chromatography equipped with TCD (Thermal Conductivity Detector) as a detector. Each product's peak area was corrected by its sensitivity to find a yield and conversion. 1,1,1,2,2-pentafluoro- 3,3-dichloropropane is hereafter indicated as 225 ca and the product tetrafluorochloropropene as 1224. In the following table-1, the content of each product in the reaction mixture was shown at every reaction temperatures.

TABLE 1

| Reaction temperature | 1224 | 225ca | others |
| --- | --- | --- | --- |
| 200° C. | 12% | 88% | 0% |
| 250° C. | 26% | 73% | 0% |
| 300° C. | 36% | 62% | 2% |
| 350° C. | 48% | 46% | 6% |

According to this result, tetrafluorochloropropene, that is an intermediate in the synthesis of 1,1,1,2,3,3-hexafluoropropane, can be obtained at a good yield and good selectivity by controlling the reaction temperature.

EXAMPLE 2

The reaction was carried out at the same conditions as those of Example 1 except a multiple oxide of cupper oxide-chromia was used as a catalyst. The mixture obtained from the reaction consists of the composition shown in the following table-2, indicating that the object product can be obtained at a good yield and good selectivity.

TABLE 2

| Reaction temperature | 1224 | 225ca | others |
| --- | --- | --- | --- |
| 200° C. | 20% | 80% | 0% |
| 250° C. | 36% | 64% | 0% |
| 300° C. | 48% | 50% | 2% |

EXAMPLE 3

The reaction was carried out at the same conditions as those of Example 1 except using 1,1,2,2,3-pentafluoro-1,3-dichloropropane as a raw material. 1,1,2,2,3-pentafluoro-1,3-dichloropropane is here indicated as 225 cb. The results are shown in the following table 3. The products are also obtained at a good yield and good selectivity.

TABLE 3

| Reaction temperature | 1224 | 225cb | others |
| --- | --- | --- | --- |
| 200° C. | 26% | 74% | 0% |
| 250° C. | 33% | 67% | 0% |
| 300° C. | 52% | 48% | 2% |
| 350° C. | 64% | 30% | 6% |

EXAMPLE 4

120 g of $Cr(NO_3)_3 \cdot 9H_2O$ was disolved in 250 ml of water, and then its hydroxide precipitation was formed by adding this solution and 200 ml of 28% ammonium hydroxide aqueous solution to 400 ml of heated water with stirring them. This precipitation was separated by filtration, then washed with pure water followed by drying, and finally burnt at 450° C. for 5 hours to produce the powder of oxide (chromium oxide). The powder was molded into a cylindrical shape, 5 mm of diameter and 5 mm height, by using a tapping-type molding machine.

Thus obtained catalyst was activated by being fluorinated in a current of the gas mixture of hydrogen fluoride and nitrogen at a temperature from 250 to 400° C. Then 10 g of the aforesaid catalyst (chromium fluoride) was filled in a reactor (20 mmφ×1000 mm) made of Hastelloy-C, and tetrafluorochloropropene (1224) obtained in Example 1 was introduced at a rate of 100 ml/min. after being vaporized in a vaporizer and at the same time HF was passed at a rate of 400 ml/min. also after being vaporized in a vaporizer.

The analysis of the products was performed similarly in Example 1. The product 1,1,1,2,3,3-hexafluoropropane is hereafter indicated as 236 ea. The result of the experiment was shown in the following table-4.

TABLE 4

| Reaction temperature | 236 ea | 1224 |
| --- | --- | --- |
| 200° C. | 15% | 85% |
| 250° C. | 35% | 65% |
| 300° C. | 45% | 55% |
| 350° C. | 50% | 50% |

From this result, it is known that the object compound can b e obtained at a good yield and good selectivity by controlling reaction temperature.

EXAMPLE 5

In a reactor made of Hastelloy-C (20 mmφ×1000 mm), 10 g of chromium oxide similarly prepared as that used in Example 1 was filled and set at the reaction temperature. And pretreatment was made by passing hydrogen at a rate of 200 ml/min. for 3 hours in advance.

Then, the 5:5 mixture of 1,1,1,2,2-pentafluoro-3,3-dichloropropane and 1,1,2,2,3-pentafluoro-1,3-dichloropropane (hereafter indicated as 225 Mix) was introduced at a rate of 100 ml/min. after being vaporized in a vaporizer.

The analysis of the products was performed in the same method as Example 1. The product was a mixture of three isomers of tetrafluorochloropropene. These are indicated here as 1224. The result is shown in the following table-5.

TABLE 5

| Reaction temperature | 1224 | 225 Mix | others |
| --- | --- | --- | --- |
| 200° C. | 21% | 79% | 0% |
| 250° C. | 28% | 72% | 0% |
| 300° C. | 41% | 57% | 2% |
| 350° C. | 55% | 49% | 6% |

From this result, if a mixture is used as a raw material, the object compound can be obtained at a good yield and good selectivity by controlling reaction temperature.

What is claimed is:

1. A method of producing 1,1,1,2,3,3-hexafluoropropane which comprises reacting 1,1,1,2,2-pentafluoro-3,3-dichloropropane, 1,1,2,2,3-pentafluoro-1,3-dichloropropane or a mixture thereof with hydrogen in the presence of a catalyst comprising at least one oxide of iron, chromium or copper to form tetrachlorofluoropropene; and then reacting the tetrachlorofluoropropene with hydrogen fluoride in the presence of a catalyst comprising a fluoride or oxyfluoride of chromium or aluminum.

2. A method according to claim 1 wherein a mixture of 1,1,1,2,2-pentafluoro-3,3-dichloropropane and 1,1,2,2,3-pentafluoro- 1,3-dichloropropane is reacted with hydrogen.

3. A method of producing tetrafluorochloropropene which comprises reacting 1,1,1,2,2-pentafluoro-3,3-dichloropropane, 1,1,2,2,3-pentafluoro-1,3-dichloropropane or a mixture thereof with hydrogen in the presence of a catalyst comprising at least one oxide of iron, chromium or copper.

4. A method according to claim 3, wherein a mixture of 1,1,1,2,2-pentafluoro-3,3-dichloropropane and 1,1,2,2,3-pentafluoro- 1,3-dichloropropane is reacted with hydrogen.

* * * * *